(12) United States Patent
Chung et al.

(10) Patent No.: US 10,754,419 B2
(45) Date of Patent: Aug. 25, 2020

(54) HYBRID POSE TRACKING SYSTEM WITH ELECTROMAGNETIC POSITION TRACKING

(71) Applicant: Google LLC, Mountain View, CA (US)

(72) Inventors: Sherk Chung, Piedmont, CA (US); Ian Atkinson, Castro Valley, CA (US); Saket Patkar, Mountain View, CA (US); Lucine Oganesian, Mountain View, CA (US); Advait Jain, Santa Clara, CA (US); Murphy Stein, San Jose, CA (US)

(73) Assignee: GOOGLE LLC, Mountain View ( * ) Notice: Subject to any disclaimer, the term of this patent is extended or adjusted under 35 U.S.C. 154(b) by 173 days.

(21) Appl. No.: 16/033,623

(22) Filed: Jul. 12, 2018

(65) Prior Publication Data

US 2020/0019231 A1 Jan. 16, 2020

(51) Int. Cl.
*G06K 9/00* (2006.01)
*G06F 3/01* (2006.01)
(Continued)

(52) U.S. Cl.
CPC .............. *G06F 3/011* (2013.01); *G01B 7/003* (2013.01); *G01S 17/08* (2013.01); *G06K 9/2027* (2013.01); *G06T 7/70* (2017.01)

(58) Field of Classification Search
CPC ........ G06F 3/011; G06F 3/012; G06F 3/0304; G06F 3/0325; G06F 3/0346; G06F 3/0338; G06F 3/01; G06F 3/017; G06F 1/1698; G06F 1/1694; A61B 2090/365; A61B 2090/0818; A61B 2034/2046; A61B 2034/2051; A61B 2034/107; A61B 2034/2055; A61B 2034/2063; A61B 5/062; A61B 34/20; G06T 7/70; G06T 17/00; G06T 19/006; G06T 2200/04; G06T 2200/08; G01B 7/003; H04B 5/0056; G01S 17/08; G01S 17/89; G01S 17/66;
(Continued)

(56) References Cited

U.S. PATENT DOCUMENTS

| | | | |
|---|---|---|---|
| 7,640,106 B1 | 12/2009 | Stokar et al. | |
| 2013/0237811 A1 | 9/2013 | Mihailescu et al. | |
| 2016/0258782 A1* | 9/2016 | Sadjadi | ................. A61B 34/20 |
| 2017/0352184 A1* | 12/2017 | Poulos | ............... G02B 27/0172 |
| 2018/0053056 A1 | 2/2018 | Rabinovich et al. | |
| 2018/0108179 A1 | 4/2018 | Tomlin et al. | |

(Continued)

OTHER PUBLICATIONS

International Search Report and Written Opinion dated Oct. 10, 2019 for corresponding PCT Application No. PCT/US2019/040515, 18 pages.

(Continued)

*Primary Examiner* — Jose L Couso

(57) ABSTRACT

A device uses a hybrid pose tracking system, whereby the hybrid pose tracking system includes both an EM pose tracking system and a secondary pose tracking system, such as a line-of-sight pose tracking system. The hybrid pose tracking system collects EM pose data from the EM tracking system indicating a relative pose between a transmitter and a receiver, and further collects from the secondary tracking system secondary pose data that is also indicative of the pose of either the transmitter or the receiver. The hybrid pose tracking system calculates a weighted combination (e.g., a weighted sum) of the EM pose data and the secondary pose data to generate a final pose for the device.

22 Claims, 9 Drawing Sheets

(51) Int. Cl.
  *G06T 7/70* (2017.01)
  *G01B 7/00* (2006.01)
  *G01S 17/08* (2006.01)
  *G06K 9/20* (2006.01)

(58) Field of Classification Search
  CPC .......... G01S 17/87; G01S 17/024; G01S 5/00;
    G01S 5/0263; G01S 5/16; G01S 5/247;
    G01S 11/14; G01S 11/12; G01S 11/02;
    G01S 13/66; G06K 9/2027; G06K
    9/3241; G06K 9/4604; G06K 9/00255;
    G06K 9/00671; G02B 27/0093; G02B
    27/017; G02B 27/0172; G02B 2027/014;
    A63F 13/235; A63F 13/25; A63F 13/00;
    A63F 13/211; A63F 13/212; A63F
    13/213; A63F 13/428; G06N 3/006
  See application file for complete search history.

(56) References Cited

U.S. PATENT DOCUMENTS

| | | | |
|---|---|---|---|
| 2019/0012835 A1* | 1/2019 | Bleyer | G06T 19/006 |
| 2019/0041979 A1* | 2/2019 | Kirchner | G01P 15/08 |
| 2019/0053858 A1* | 2/2019 | Kapoor | G01B 11/002 |
| 2019/0187779 A1* | 6/2019 | Miller | A63F 13/235 |
| 2019/0242952 A1* | 8/2019 | Schneider | G01R 33/025 |
| 2019/0250218 A1* | 8/2019 | Anfiteatro | G06F 3/017 |

OTHER PUBLICATIONS

Perrson, L. et al., "On-line Metrics for Assessment of Fused Tracking Performance," Oceans 2011 IEEE—Spain; Jun. 6, 2011, XP032040249, ISBN: 978-1-4577-0086-6, 8 pages.

He et al., "An Inertial and Optical Sensor Fusion Approach for Six Degree-of-Freedom Pose Estimation", Sensors, vol. 15, Jul. 8, 2015, 18 pages.

* cited by examiner

HYBRID POSE TRACKING SYSTEM WITH ELECTROMAGNETIC POSITION TRACKING

BACKGROUND

Field of the Disclosure

The present disclosure relates generally to pose tracking systems and more particularly to electromagnetic (EM) tracking systems.

Description of the Related Art

Pose tracking systems are increasingly used in a variety of different devices to identify relative positions or orientations between objects. For example, a pose tracking system can be used to provide positional input from an accessory to a computing device, or in a virtual reality display system to identify relative positions between a display device (e.g. a head mounted display) and a handheld controller, thereby allowing a user to manipulate items in a virtual environment. Examples of such pose tracking systems include line-of-sight pose tracking systems, wherein the relative position is identified based on a transmitted line-of-sight signal such as light or sound, and include pose tracking systems that use near-field electromagnetic fields ("EM tracking systems"). However, each of these different types of pose tracking systems can be negatively impacted by the presence of objects in the surrounding environment. For example, some objects can interfere with line-of-sight signals, while other objects can interfere with EM fields. Such interference can cause errors in position tracking, and therefore negatively impact the user experience.

BRIEF DESCRIPTION OF THE DRAWINGS

The present disclosure may be better understood, and its numerous features and advantages made apparent to those skilled in the art by referencing the accompanying drawings. The use of the same reference symbols in different drawings indicates similar or identical items.

DETAILED DESCRIPTION

FIGS. 1-9 illustrate techniques for tracking a pose (position, orientation, or both) of a device using a hybrid pose tracking system, whereby the hybrid pose tracking system includes both an EM pose tracking system and a secondary pose tracking system, such as a line-of-sight pose tracking system. The hybrid pose tracking system collects EM pose data from the EM tracking system indicating a relative pose between a transmitter and a receiver, and further collects from the secondary tracking system secondary pose data that is also indicative of the pose of either the transmitter or the receiver. The hybrid pose tracking system calculates a weighted combination (e.g., a weighted sum) of the EM pose data and the secondary pose data to generate a final pose for the device. By employing both the EM pose tracking system and the secondary pose tracking system, and by adjusting the weights associated with the pose data generated by each pose tracking system, the hybrid pose tracking system provides for accurate pose tracking in a variety of different environments, thereby improving the user experience.

To illustrate via an example, the hybrid pose tracking system can be employed as part of a portable display system that can be carried or moved in a variety of different, and unknown (that is, not predefined) environments. These different environments can include objects that interfere with one or both of an EM pose tracking system or a secondary pose tracking system (e.g. a line-of-sight pose tracking system). For example, some environments can include metal objects that interfere with the EM field generated by the EM pose tracking system. Other environments can include objects, such as tables or windows, that block or otherwise interfere with line-of-sight signals used by the secondary pose tracking system. However, because the hybrid pose tracking system employs both EM pose tracking and secondary pose tracking, the system can identify accurate poses in these different environments, thereby supporting an improved user experience.

It will be appreciated that the term "secondary" is used herein to differentiate non-EM pose tracking systems, and associated signals, from non-EM pose tracking systems for clarity of description, and is not intended to convey relative importance or frequency of use of each tracking system, nor the weights applied to the pose data generated by each pose tracking system. For example, and as described further herein, for some devices and systems, and for some operating conditions of some devices and systems, a higher weight is applied to pose data generated by the non-EM pose tracking system than the weight applied to pose data generated by the EM pose tracking system.

Figure 1:
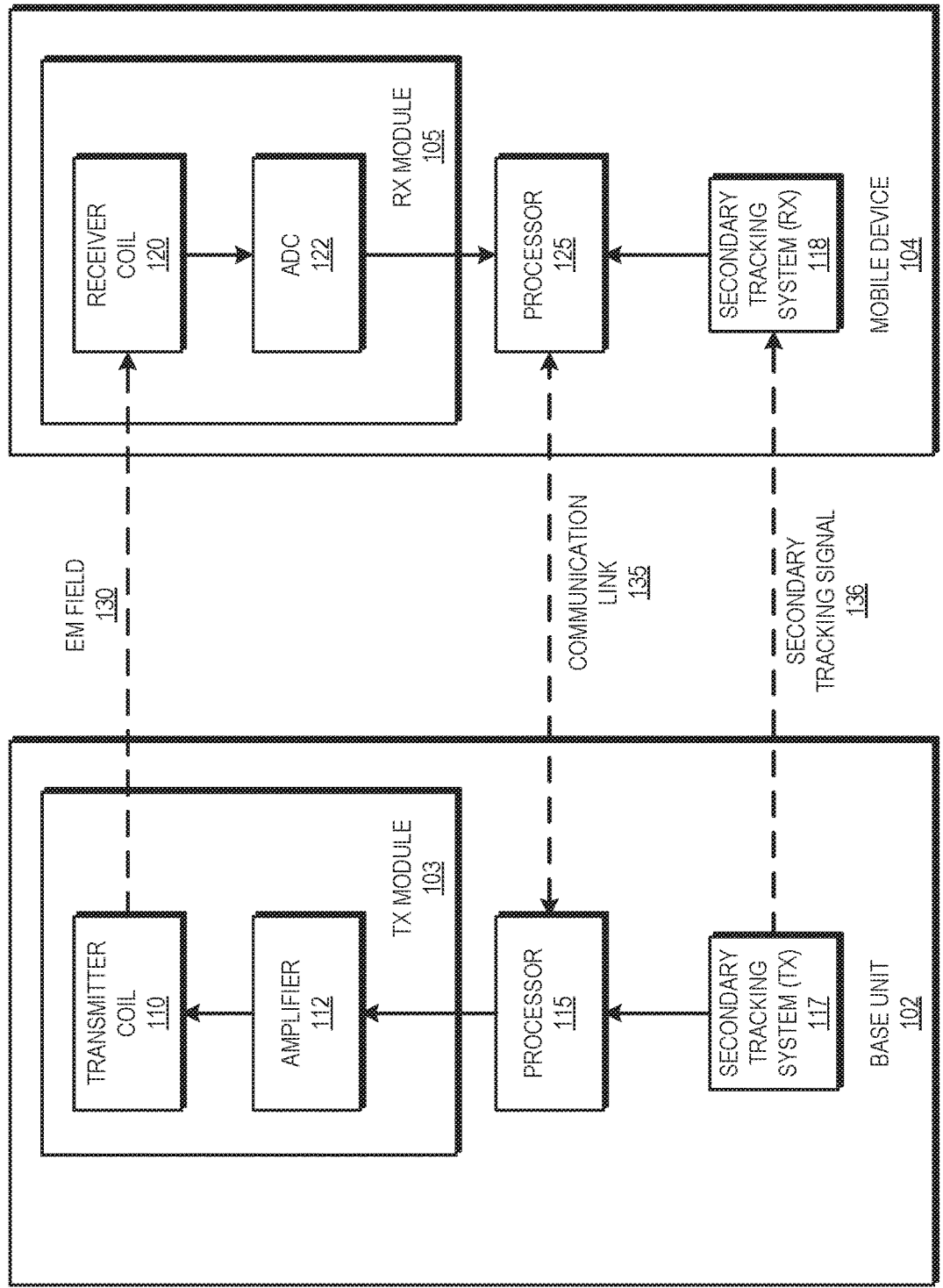
FIG. 1 is a block diagram of a pose tracking system employing both an EM pose tracking system and a secondary tracking system, such as a line-of-sight pose tracking system, in accordance with at least one embodiment.

Turning to the Figures, FIG. 1 illustrates a tracking system 100 that employs both an EM tracking system and a secondary tracking system to identify poses of one or more electronic devices.

In the depicted example, the tracking system 100 includes a base unit 102 and a mobile device 104, where either base unit or mobile device could be mobile in some embodiments. As described further herein, the tracking system 100 is generally configured to identify poses of either the base unit 102 or the mobile device 104 based on a weighted combination of EM poses (poses generated based on an EM field 130 as described further herein) and secondary poses (poses generated based on a secondary tracking signal 136 as described further herein). The tracking system 100 can therefore be incorporated into a variety of devices and systems that employ pose identification features. For example, in some embodiments the tracking system 100 is incorporated in a virtual reality (VR) to identify a relative pose between an HMD and a hand-held controller. Thus, in some configurations, the base unit is the HMD and the mobile unit is the hand-held controller. In other configurations, the base unit is a device separate from the HMD (such as an accessory or a base-station).

To generate an EM pose, the tracking system 100 generates the EM field 130, measures a magnitude and/or phase of the generated EM field 130 (referred to herein generally as "EM data"), and computes a relative pose based on the corresponding EM data. In the illustrated embodiment, the EM field 130 is generated by the base unit 102 and the EM data is read at the mobile device 104. It will be appreciated that other configurations are possible, including the EM field 130 being generated by the mobile device 104 and the EM data being read at the base unit 102. To support generation of the EM field, the base unit 102 includes a Tx module 103, whereby the Tx module 103 includes a transmitter coil 110 and an amplifier 112. In some embodiments, the transmitter coil 110 is a tri-axis coil generally configured to generate the EM field 130 at a strength, referred to herein as the transmit power, wherein the transmit power is based on electrical power provided by the amplifier 112 to the transmitter coil 110. The amplifier 112 is a programmable amplifier generally configured to generate the electrical power at a magnitude based on received control signaling as described further below. Thus, the transmit power for the EM field 130 is a programmable value that is controlled at the base unit 102 as described further below.

To support reading of EM data, the mobile device 104 includes an Rx module 105 having a receiver coil 120 and an analog-to-digital converter (ADC) 122. In some embodiments, the receiver coil 120 is a tri-axis coil configured to generate an analog electrical signal having a magnitude and/or phase indicative of a detected EM field 130. The ADC 122 is generally configured to receive the generated analog signal and convert the analog signal to a digital value indicative of the analog signal, and therefore indicative of the detected EM field 130. Thus, in the example of FIG. 1, the digital values generated by the ADC 122 are EM data that can be used for pose identification as described further below.

To support generation of secondary poses, the base unit 102 includes a secondary tracking system transmitter (Tx) module 117 that is generally configured to generate a secondary tracking signal 136. The type of signal corresponding to the secondary tracking signal can vary depending on the specific implementation of the tracking system 100. For example, in some embodiments the secondary tracking signal is a light-based signal, such as a laser, LED light, and the like. In other embodiments, the secondary tracking signal is a sonic signal, such as an ultrasonic signal. In still other embodiments the secondary tracking signal is radio frequency (RF) signal. And in other embodiments the secondary tracking signal is not transmitted but rather is passive, such as a picture of a pattern that can be tracked by a camera. The mobile device 104 includes a secondary tracking system receiver (Rx) module 118 generally configured to identify a signal strength or other characteristic of the secondary tracking signal and, based on the signal strength or other characteristic, generate secondary pose data.

It will be appreciated that while in the illustrated embodiment of FIG. 1 the secondary tracking system Tx module 117 is affixed to the base unit 102 with the Tx module 103, and the secondary tracking system Rx module 118 is affixed to the mobile device 104 with the Rx module 105, in other embodiments other configurations of the different Tx and Rx modules are possible without departing from the scope of the present disclosure. For example, and as described further herein, in some embodiments the Tx module 117 is affixed to the mobile device 104 with the Rx module 105 and the Rx module 118 is affixed to the base unit 102 with the Tx module 103. In still other embodiments, one or more of the Tx module 117 and the Rx module 118 are located remotely from both the base unit 102 and the mobile device 104 at a third device, such as a separate secondary base station or separate secondary receiver.

To support pose identification (that is, identification of poses of either the base unit 102 or the mobile device 104) the base unit 102 and the mobile device 104 include processors 115 and 125, respectively. The processors 115 and 125 are general-purpose or application-specific processors generally configured to execute instructions (e.g., computer programs) in order to carry out specified tasks. In some embodiments, at least one of the processors 115 and 125 executes instructions to identify a pose of the base unit 102 or the mobile device 104 based on a weighted combination of the EM data provided by the ADC 122 and the secondary pose data generated by the secondary tracking system Rx module 118. In other embodiments, a different processor on an external system (such as a PC computer, for example) is used to compute pose. In one example, in some embodiments, the processor 125 identifies the pose based on the following formula:

$$pose_{final} = (W_{em} * pose_{em} + W_{secondary} * pose_{secondary}) / (W_{em} + W_{secondary})$$

where $W_{em}$ is the weight applied to the pose computed from the EM signal, $pose_{em}$ is the pose computed from the EM data, $W_{secondary}$ is the weight applied to the pose computed from the secondary tracking signal 136, and $pose_{secondary}$ is the pose computed from the secondary tracking signal.

In some embodiments, the processor 125 can adjust one or both of the weights $W_{em}$ and $W_{secondary}$ based on one or more factors, such as detected degradation in one or both of the EM data and the secondary pose data, detected changes in operating conditions of the tracking system 100, and the like, or a combination thereof. For example, in at least one embodiment the processor 125 initially sets the weights $W_{em}$ and $W_{secondary}$ to corresponding initial values, such as zero and one, respectively. In response to detecting degradation in the secondary pose data, the processor 125 adjusts the weights $W_{em}$ and $W_{secondary}$ to specified adjusted values, such as 0.9 and 0.1, respectively. In response to determining that the secondary pose data is no longer degraded, the processor 125 returns the weights $W_{em}$ and $W_{secondary}$ to their respective specified initial values. Thus, the tracking system 100 can adjust the weights to respond to data degradation and other changing conditions, thereby improving overall accuracy of the generated poses, and in turn improving the user experience.

In other embodiments, the weights $W_{em}$ and $W_{secondary}$ are optimized using a Bayesian inference model and by computing a joint probability distribution between the EM and secondary pose measurements using Kalman filters. In other embodiments, the secondary tracking system is used most of the time while the EM system is maintained in a low-power state, such as an off state or a sleep state. When the secondary tracking system degrades, the EM tracking system is powered up and weighted to contribute to the combined pose measurements. And in other embodiments the EM system tracking system is used most of the time while the secondary tracking system is kept in a low-power state, and turned on when degradation of the EM poses is detected.

In addition, in the example of FIG. 1 the processors 115 and 125 are connected via a communication link 135 to support communication of EM data, secondary pose data, identified poses, or other information. For example, in some embodiments the processor 125 identifies poses based on the EM data and secondary pose data and communicates the identified poses to the processor 115. In other embodiments, the processor 125 communicates the EM data and the secondary pose data to the processor 115, which identifies poses based on the weighted combination. The communication link 135 can be a wired communication link, a wireless communication link (e.g. Bluetooth), and the like, or a combination thereof. In other embodiments, the EM data and the secondary pose data can be sent to a third processor (not pictured) where the pose is computed from the weighted combination of the EM data and the secondary pose data.

In some embodiments, one or more of the processors 115 and 125 (or a third processor not shown at FIG. 1) execute additional sets of instructions to use the poses determined based on the EM data and the secondary pose data. For example, in some embodiments wherein the base unit 102 is an HMD, and the mobile device 104 is a hand-held controller, the processor 115 can execute sets of instructions to display a virtual reality environment to a user, and employ the identified poses to determine a location of the hand-held controller in the virtual reality environment, thereby allowing the user to interact with the virtual reality environment using the hand-held controller.

Figure 2:
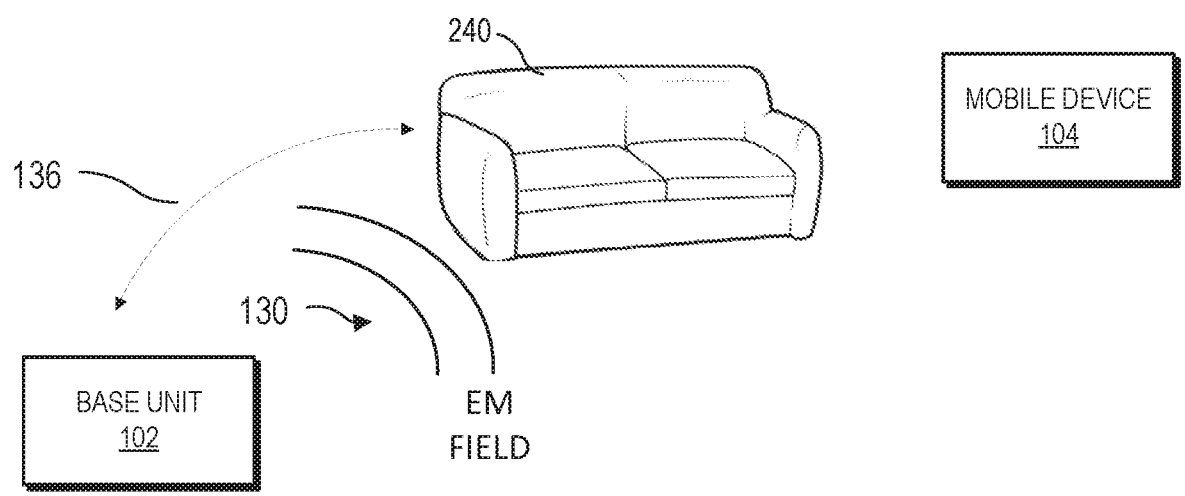
FIG. 2 is a diagram illustrating an example of an object in the environment of the pose tracking system interfering with the secondary tracking system in accordance with at least one embodiment.
Figure 3:
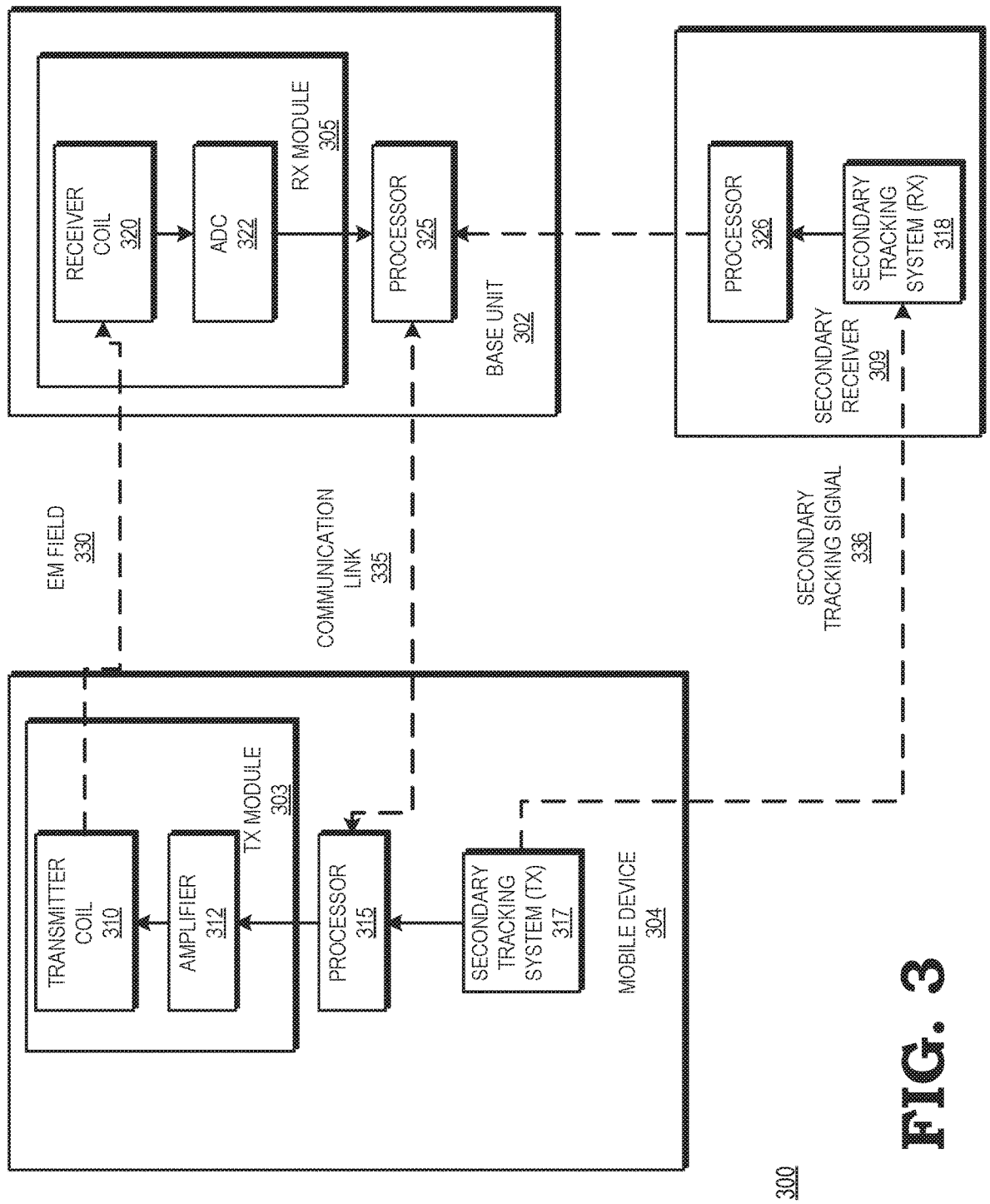
FIG. 3 is a block diagram of another pose tracking system employing an EM pose tracking system and a secondary tracking system having a secondary receiver in accordance with at least one embodiment.

As noted above, the tracking system 100 can adjust the weights applied to the EM pose data and the secondary pose data based on data degradation or other changing conditions. An example is illustrated at FIG. 2 in accordance with at least one embodiment. In the depicted example, an object 240 is located between the base unit 102 and the mobile device 104. For purposes of the example, it is assumed that the object 240 at least partially blocks or otherwise interferes with the secondary tracking signal 136 but has a lesser impact on the EM field 130. Thus, under the conditions illustrated at FIG. 2, the EM pose data is likely to generate more accurate poses than the secondary pose data. Accordingly, in response to detecting degradation in the secondary pose data, the tracking system 100 can increase the weight $W_{em}$ and decrease the weight $W_{secondary}$ thereby giving the EM pose data a greater influence on the final pose. The EM tracking system 100 thus supports improved pose accuracy under a variety of conditions and environments.

As noted above, the techniques described herein can be employed at tracking systems having any of a variety of configurations and secondary tracking systems. An example of a different configuration is illustrated by tracking system 300 at FIG. 3 in accordance with at least one embodiment. In the illustrated example, the tracking system 300 includes a base unit 302 and a mobile device 304. The base unit 302 includes an Rx module 305 having an EM receiver coil 320 and an ADC 322, and also includes a processor 325. The mobile device 304 includes an EM Tx module 303 having a transmitter coil 310 and an amplifier 312, and also includes a processor 315 and a secondary tracking system Tx module 317. Each of the above-referenced modules performs similar or analogous operations to those described above with respect to the tracking system 100 of FIG. 1. However, the tracking system 300 differs from the tracking system 100 by placing the EM Tx module 303 at the mobile device 304 and the EM Rx module 305 at the base unit 102.

In addition, the tracking system 300 locates the secondary tracking system Rx module at a secondary receiver 309 that is separate, and located remotely, from the base unit 302 and the mobile device 304. The secondary receiver 309 includes a processor 326 generally configured to generate secondary poses based on secondary pose data generated by the secondary tracking system Rx module 318. In the depicted example, the processor 326 communicates with the processor 325, and together the two processors determine a final pose based on a weighted combination of the EM pose data and secondary pose data in similar fashion to that described above with respect to FIG. 1. In other embodiments, other components, including any receiver or transmitter of either the EM tracking system or the secondary tracking system can be located at a separate base station or other module located remotely from the base unit 302 and the mobile device 304.

Figure 4:
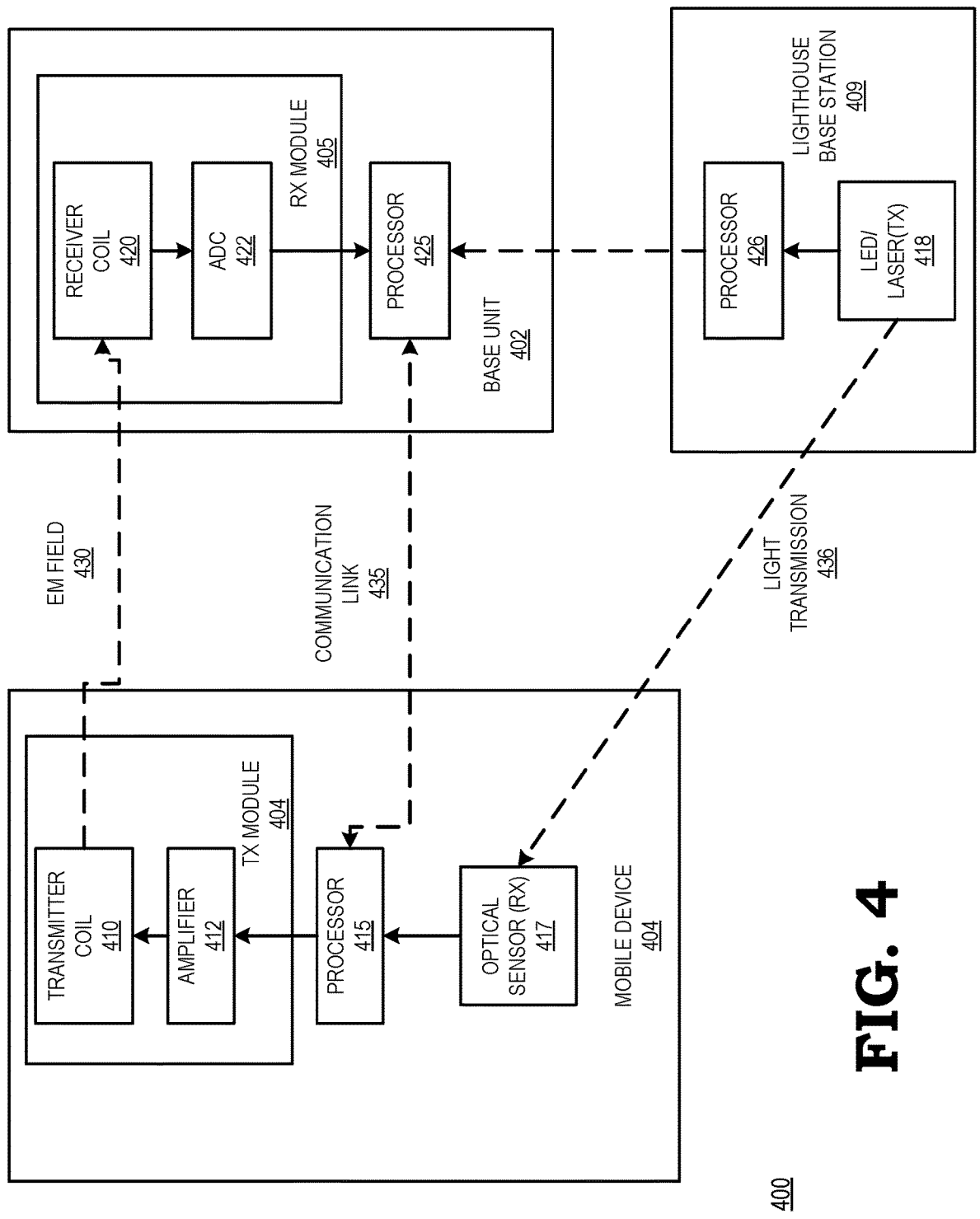
FIG. 4 is a block diagram of a pose tracking system employing an EM pose tracking system and a lighthouse pose tracking system in accordance with at least one embodiment.

As noted above, the secondary pose tracking system can be any of a number of pose tracking systems, including a line-of-sight pose tracking system that generates secondary pose data based on a line-of-sight signal, such as a light signal, sonic signal, RF signal, and the like. Examples of tracking systems employing different types of secondary tracking systems are illustrated at FIGS. 4-7. FIG. 4 depicts a tracking system 400 employing an EM pose tracking system and a lighthouse pose tracking system in accordance with at least one embodiment.

In the illustrated example, the tracking system 400 includes a base unit 402 and a mobile device 404. The base unit 402 includes a Rx module 405 having an EM receiver coil 420 and an ADC 422, and also includes a processor 425. The mobile device 404 includes an EM Tx module 409 having a transmitter coil 410 and an amplifier 412, and also includes a processor 415. Each of the above-referenced modules performs similar or analogous operations to those described above with respect to the tracking system 300 of FIG. 3.

With respect to the secondary tracking system, the tracking system 400 includes a lighthouse base station 403 having an LED/laser transmitter 418 and a processor 426. In addition, the secondary tracking system includes an optical sensor (also known as an optical receiver) 417 located at the mobile device 404. In operation, the LED/laser transmitter 418 emits an LED pulse to denote the start of a measurement frame, and then rotates one or more lasers. The optical sensor 417 measures time between an LED flash and the rotating laser hits to determine angles relative to the lighthouse base station 403. The optical sensor 417 forwards the timing information to the processor 415 which can triangulate a position (the secondary pose) from the timing data.

Figure 5:
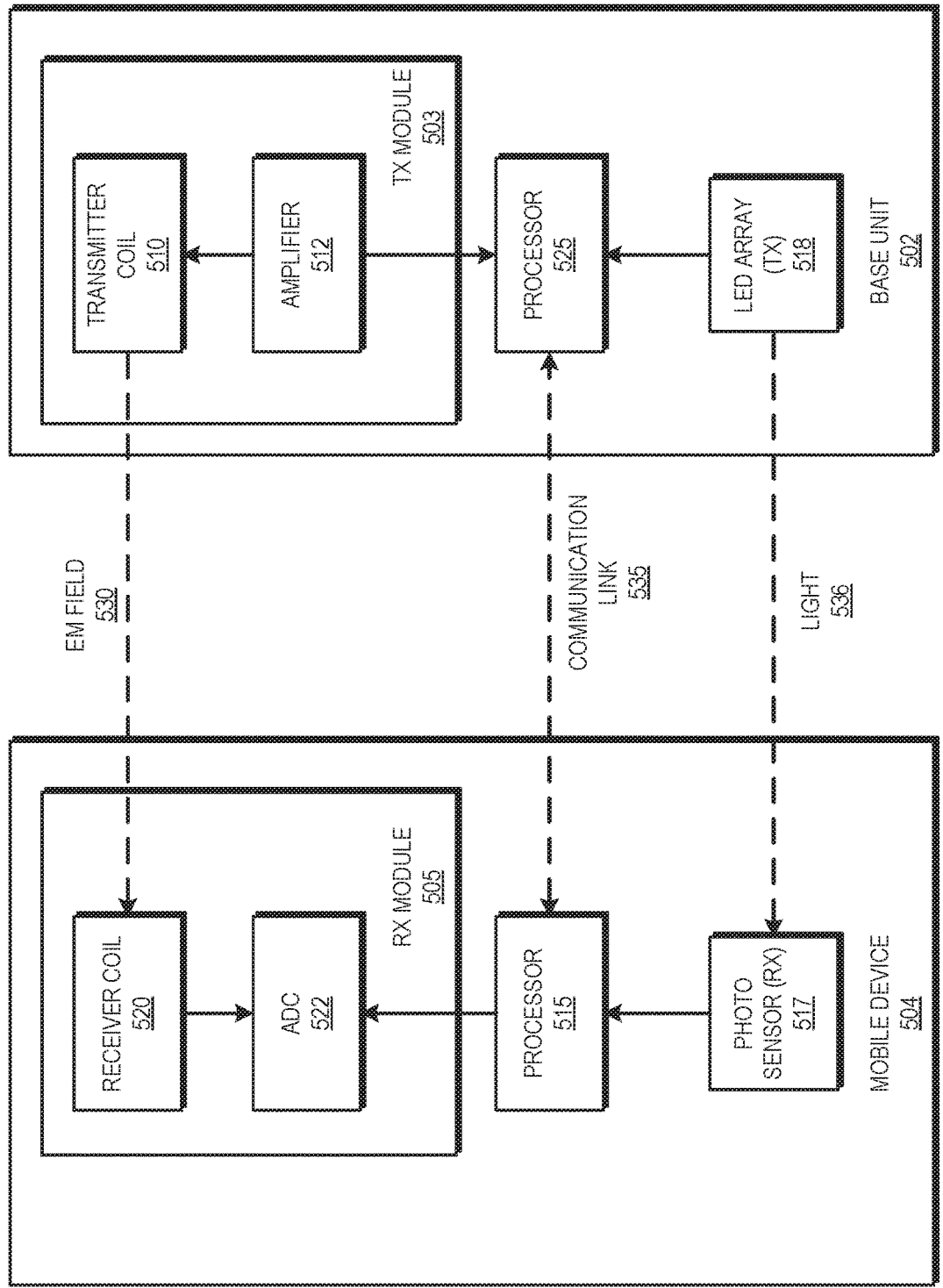
FIG. 5 is a block diagram of a pose tracking system employing an EM pose tracking system and an LED constellation pose tracking system in accordance with at least one embodiment.

FIG. 5 illustrates a pose tracking system 500 employing an EM pose tracking system and an LED constellation pose tracking system in accordance with at least one embodiment. In the depicted embodiment, the tracking system 500 includes a base unit 502 and a mobile device 504. The mobile device 504 includes an Rx module 505 having an EM receiver coil 520 and an ADC 522, and also includes a processor 515. The base unit 502 includes an EM Tx module 503 having a transmitter coil 510 and an amplifier 512, and also includes a processor 525. Each of the above-referenced modules performs similar or analogous operations to those described above with respect to the tracking system 100 of FIG. 1.

With respect to the secondary tracking system the tracking system 500, the base unit 502 includes an LED array (transmitter) 518 that contains one or more LEDs, and the mobile device 504 includes a photosensor (receiver) 517 the includes one or more photosensitive elements. In operation, the LED array 518 generates modulated light 536. The photosensor 517 is a photo-diode, charge-coupled device (CCD) array, or other photosensor that records the light 536. The processor 515 calculates a secondary pose based on the recorded light.

Figure 6:
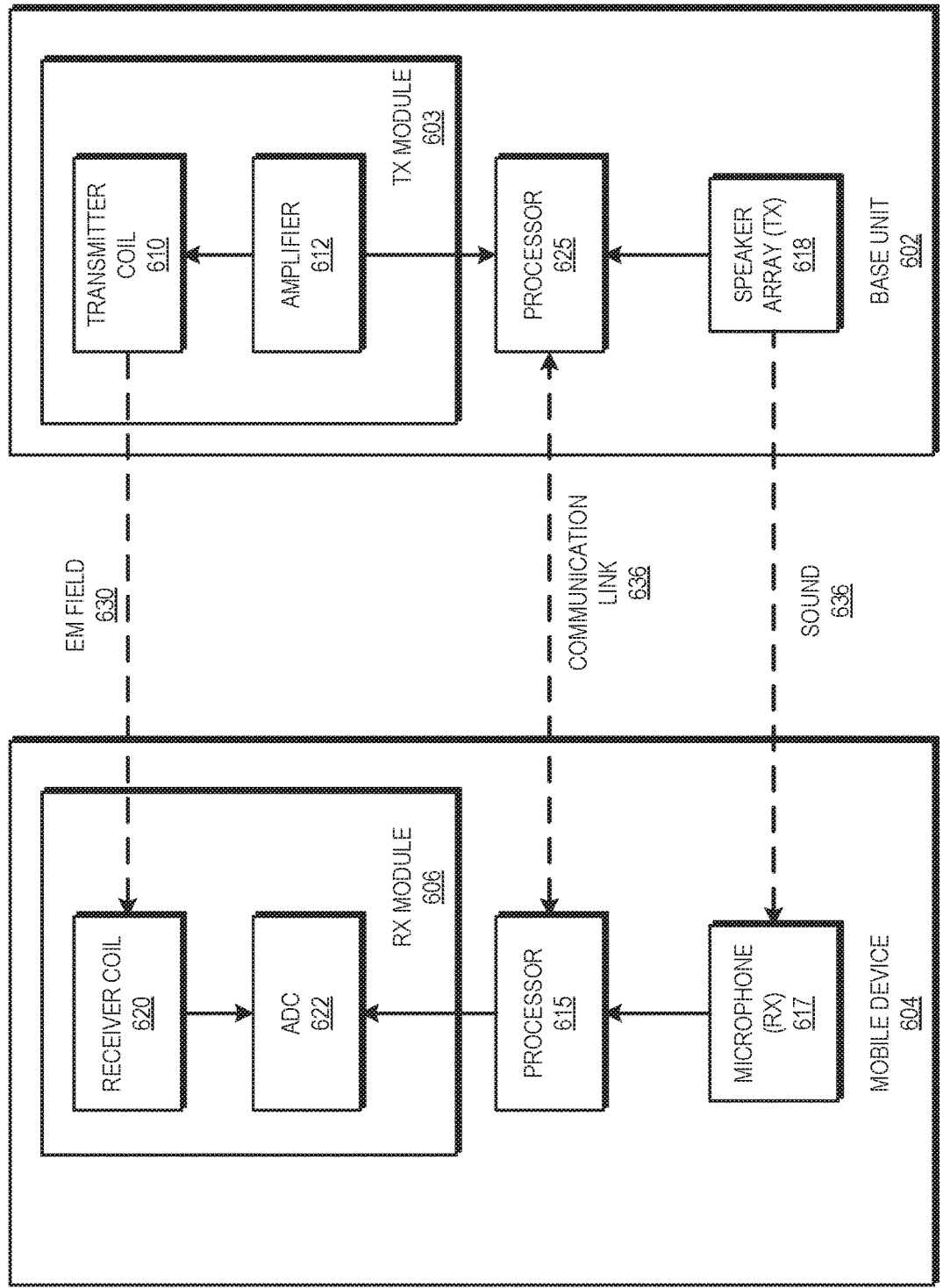
FIG. 6 is a block diagram of a pose tracking system employing an EM pose tracking system and an ultrasonic pose tracking system in accordance with at least one embodiment.

FIG. 6 illustrates a pose tracking system 600 employing an EM pose tracking system and an ultrasonic pose tracking system in accordance with at least one embodiment. In the depicted embodiment, the tracking system 600 includes a base unit 602 and a mobile device 604. The mobile device 604 includes a Rx module 605 having an EM receiver coil 620 and an ADC 622, and also includes a processor 615. The base unit 602 includes an EM Tx module 603 having a transmitter coil 610 and an amplifier 612, and also includes a processor 625. Each of the above-referenced modules performs similar or analogous operations to those described above with respect to the tracking system 100 of FIG. 1.

With respect to the secondary tracking system, the base unit 602 includes a speaker array (transmitter) 618 that contains one or more speakers, and the mobile device 604 includes a microphone array (receiver) 617 that includes one or more microphones. In operation, the speaker array 518 generates ultrasonic sound 636. The microphone array 617 records the sound 636, and the processor 615 processes the captured audio data to determine the time it took for the audio wave to travel from the speaker to the microphone. The "time of flight" of the audio wave can be converted into distance since the speed of sound is known, and by computing three or more distances the processor 615 can triangulate the position of the base unit 602 relative to the mobile device 604, thereby generating secondary poses. The secondary tracking system can further implement carrier phase tracking, by compensating for clock error between the base unit 602 and the mobile device 604 and by adjusting the speed of sound based on altitude or temperature, thus improving the accuracy of the secondary poses.

Figure 7:
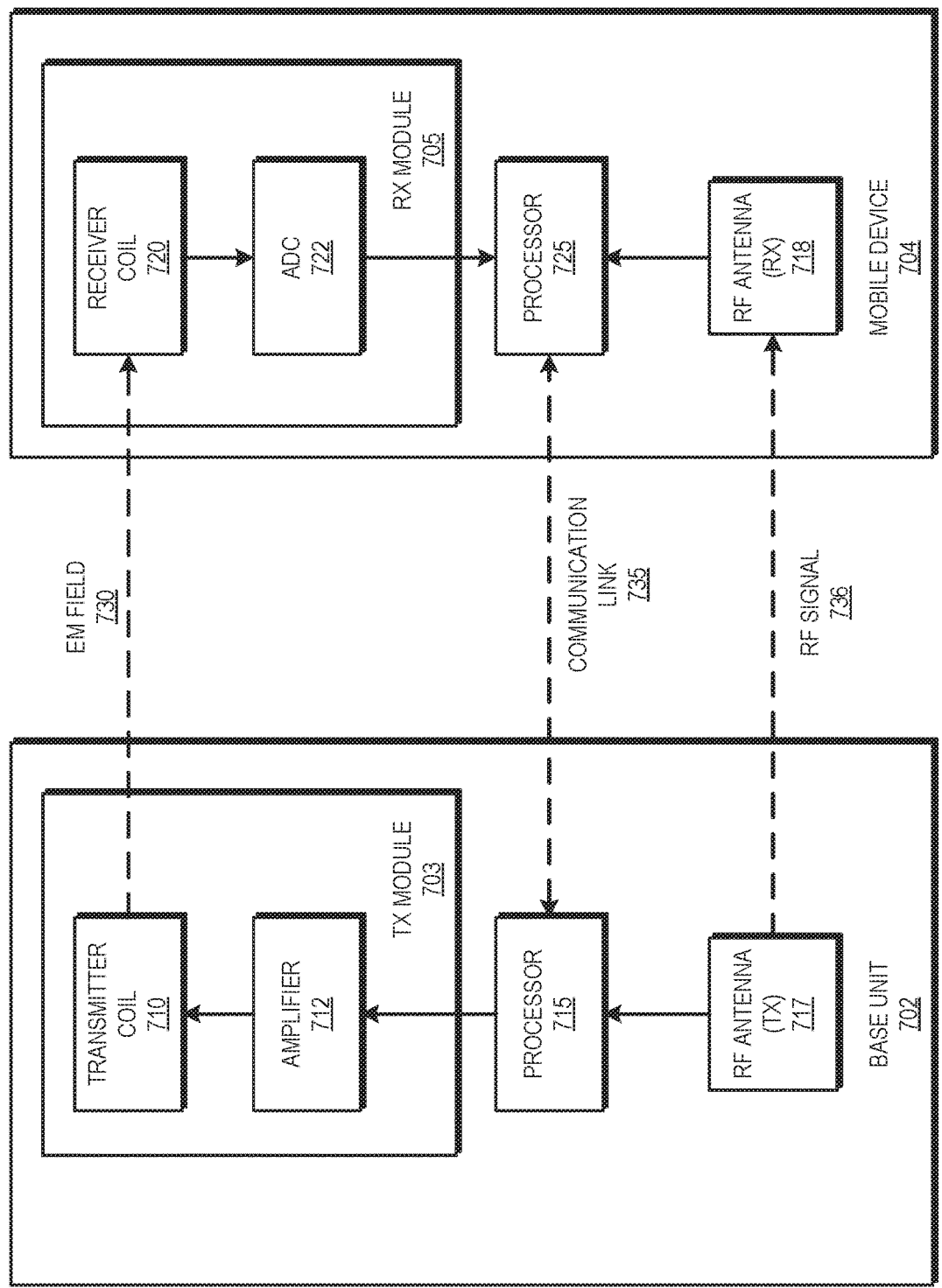
FIG. 7 is a block diagram of a pose tracking system employing an EM pose tracking system and a radio-frequency (RF) pose tracking system in accordance with at least one embodiment.

FIG. 7 illustrates a pose tracking system 700 employing an EM pose tracking system and a radio frequency (RF) pose tracking system in accordance with at least one embodiment. In the depicted embodiment, the tracking system 700 includes a base unit 702 and a mobile device 704. The mobile device 704 includes an Rx module 705 having an EM receiver coil 720 and an ADC 722, and also includes a processor 715. The base unit 702 includes an EM Tx module 703 having a transmitter coil 710 and an amplifier 712, and also includes a processor 725. Each of the above-referenced modules performs similar or analogous operations to those described above with respect to the tracking system 100 of FIG. 1.

With respect to the secondary tracking system, the base unit 702 includes one or more RF antennas (transmitter) 717 and the mobile device 704 includes one or more RF antennas (receiver) 718. In operation, the transmitter 717 generates an RF signal 736. The receiver 718 measures an RF field resulting from the signal 736. Based on these measurements, the processor 725 detects phases in the RF field, and uses the detected phases to compute a range between the base unit 702 and the mobile device 704. Based on computed ranges, the processor 725 can compute a pose of the mobile device 704 relative to the base unit 702, thereby generating secondary poses.

In at least one embodiment, the secondary tracking system uses video cameras for accurate pose estimation. A camera on the base unit 702 captures video frames using, in at least one embodiment, a wide-angle lens for increased field of view. The processor 715 processes the captured video frames to generate pose estimates of the mobile device 704 when it is within the field of view of the camera. In some embodiments the processor 715 extracts features (such as corners, edges, known shapes, etc.) of the mobile device 704, and uses the extracted feature to generate secondary poses. In other embodiments, the processor 715 processes the pixels from the captured video frames directly using a machine learning model to estimate pose of the mobile device 704.

In still other embodiments, the camera is located at the mobile device 704 and captures video images of its surroundings. In these embodiments, the processor 725 can process the captured video images to track features of the environment surrounding the mobile device 704 to generate secondary poses.

Figure 8:
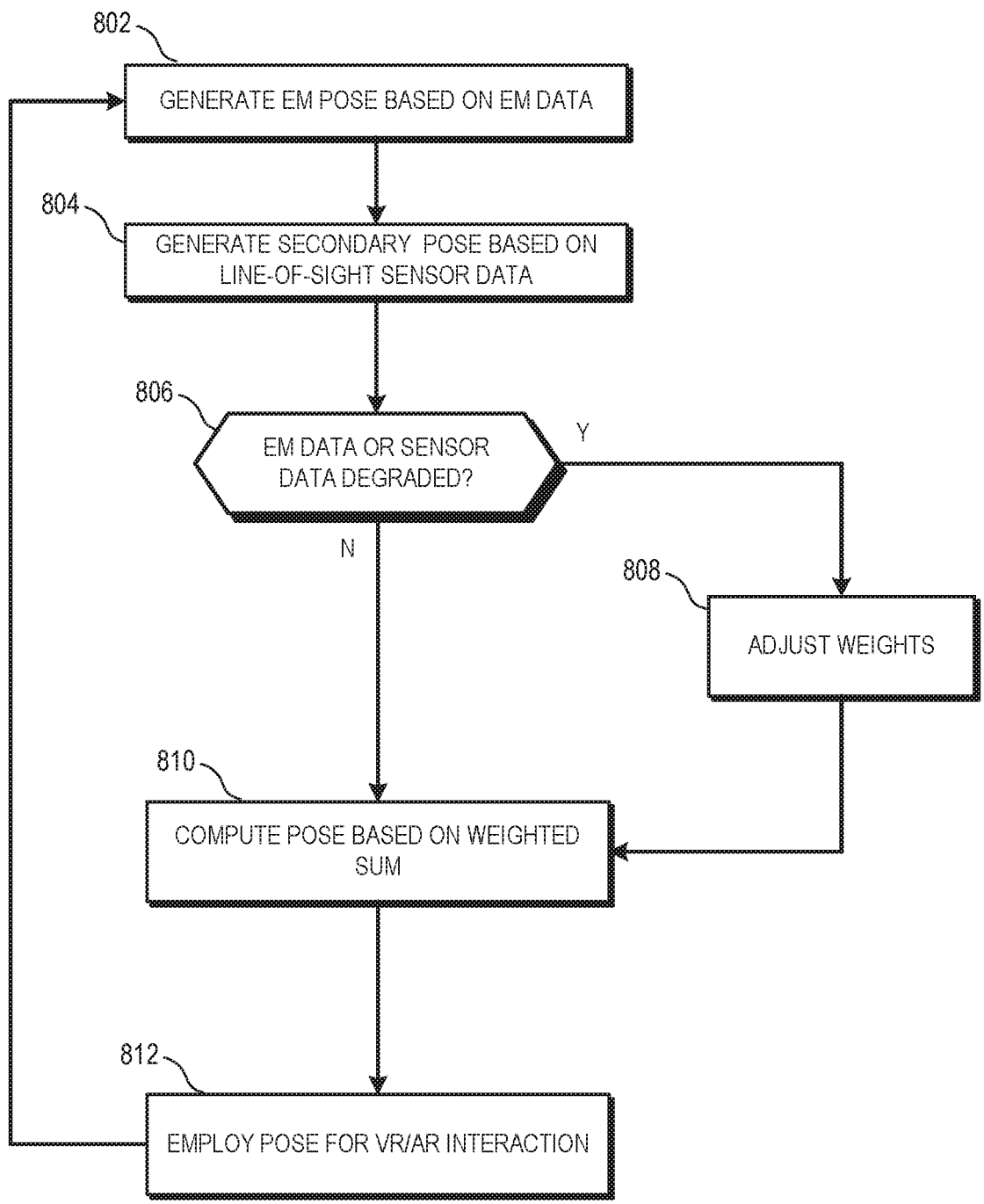
FIG. 8 is a flow diagram of a method of using a combination of an EM pose tracking system and a secondary pose tracking system to identify a pose of a device in accordance with at least one embodiment.

FIG. 8 is a flow diagram of a method 800 of a device using a combination of an EM pose tracking system and a secondary pose tracking system to identify a pose of a device in accordance with at least one embodiment. At block 802, the EM pose tracking system generates an EM pose based on EM data. At block 804, the secondary pose tracking system generates a secondary pose based on line-of-sight sensor data. In some embodiments, the secondary pose tracking system employs one of the line-of-sight tracking systems described above with respect to FIGS. 1-7 to generate the secondary pose.

At block 806, a processor of the device determines if either the EM data or the line-of-sight sensor data is degraded. In some embodiments, the processor identifies degradation based on one or more of a detected amount of noise in the corresponding data, an amount of variation in the data over a threshold amount of time, a detected signal strength associated with the data, and the like. In response to detecting that neither the EM data nor the sensor data is degraded, the method flow moves to block 810 and the processor computes a combined pose based on a weighted sum of the EM pose and the secondary pose.

Returning to block 806, in response to determining that one of the EM data and the secondary sensor data is degraded, the method flow moves to block 808 and the processor adjusts the weights used to compute the combined pose. For example, the processor can adjust the weights to reduce or substantially eliminate the influence of the pose associated with the degraded data. Thus, if the EM data is degraded, the processor can reduce the weight associated with the EM pose. In some embodiments, the processor continues to monitor the quality of both the EM data and the sensor data and, in response to an improvement in the quality of the degraded data can return the weights used to compute the combined pose to a specified nominal level.

After the weights have been adjusted at block 808, the method flow moves to block 810 and the processor computes the combined pose based on a weighted sum using the adjusted weights. From block 810, the method flow proceeds to block 812 and the device uses the combined pose to support user interaction with virtual reality (VR) or augmented reality (AR) environment. For example, the device can use the pose to support a user moving or selecting objects in the VR/AR environment.

Figure 9:
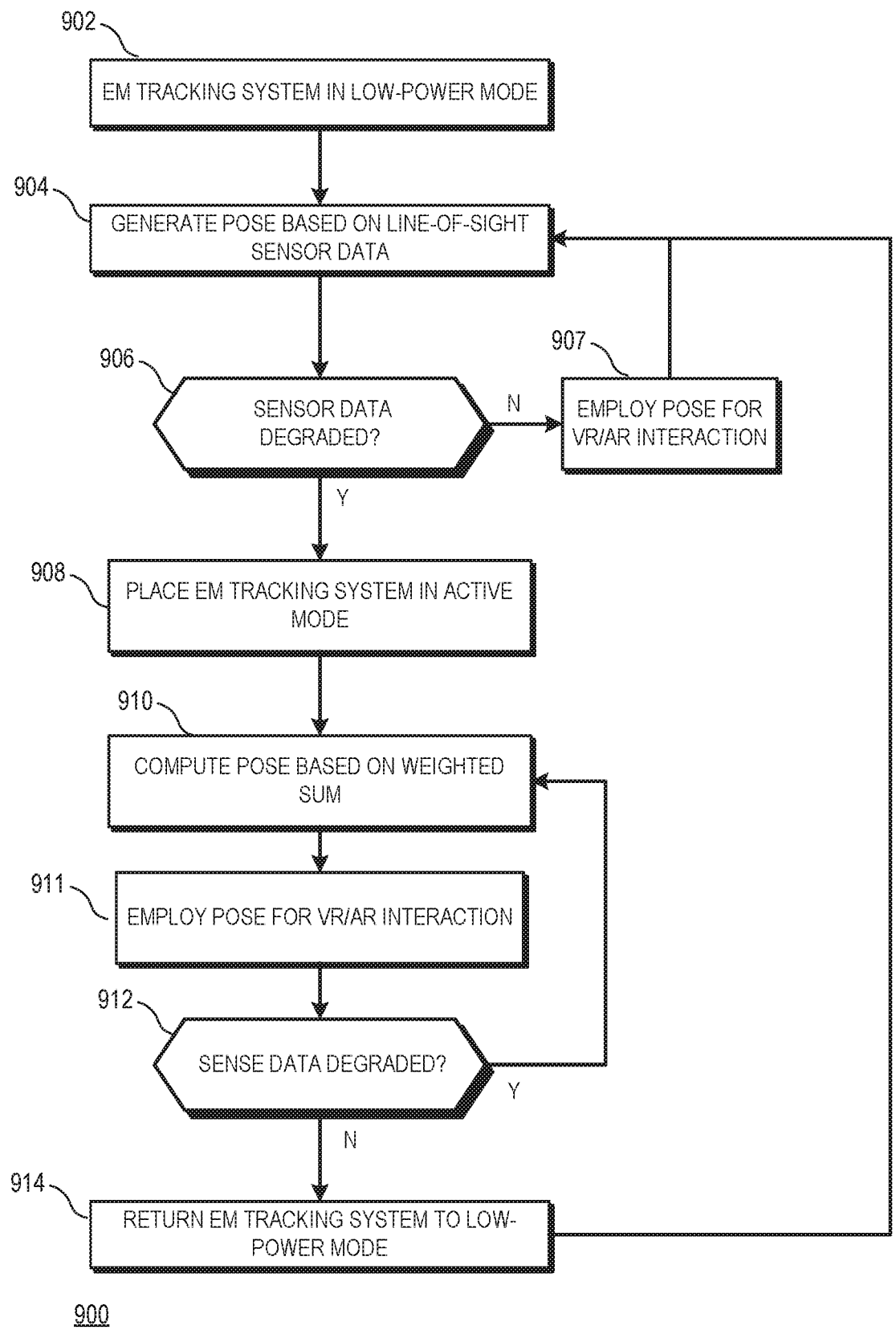
FIG. 9 is flow diagram of a method of changing a power mode of an EM pose tracking system based on degradation of secondary pose data generated by a secondary pose tracking system in accordance with at least one embodiment.

FIG. 9 is a flow diagram of a method of 900 of changing a power mode of an EM pose tracking system based on degradation of secondary pose data generated by a secondary pose tracking system of a device in accordance with at least one embodiment. At block 902 the EM tracking system is in a low-power mode, such as an off mode or a sleep mode. At block 904 a processor of the device generates a secondary pose based on line-of-sight sensor data from the secondary pose tracking system. At block 906 the processor determines if the line-of-sight sensor data is degraded. If not, the method flow proceeds to block 907 and the device uses the pose to support user interaction with virtual reality (VR) or augmented reality (AR) environment. The method flow returns to block 904. Thus, while the line-of-sight sensor data maintains a threshold level of quality, the device maintains the EM tracking system in the low-power mode and generates poses based only on the line-of-sight sensor data.

Returning to block 906, if the line-of-sight sensor data is degraded, the method flow proceeds to block 908 and the device increases power supplied to the EM tracking system, thereby placing the EM tracking system in an active mode. In the active mode, the EM tracking system begins generating EM poses as described above. At block 910 the processor computes a pose based on a weighted sum of EM poses and secondary poses as described above. At block 911 the device uses the combined pose to support user interaction with virtual reality (VR) or augmented reality (AR) environment.

The method flow proceeds to block 912 and the processor determines if the line-of-sight sensor data is still degraded. If so, the method returns to block 910 and the processor continues to compute poses based on weighted sums of the EM poses and the secondary poses. In response to determining, at block 912, that the line-of-sight sensor data is no longer degraded, the method flow moves to block 914 and the processor reduces power supplied to the EM tracking system, thereby returning the EM tracking system to the low-power mode. The method flow returns to block 904.

In other embodiments, a device implements a method similar to method 900, but with the secondary pose tracking system initially in a low power mode and the EM pose tracking system generating EM poses. The device places the secondary pose tracking system in an active mode in response to detecting a degradation in the EM pose data generated by the EM pose tracking system. While the secondary pose tracking system is in the active mode, the device generates poses based on a weighted combination of EM poses and secondary poses as described above.

In some embodiments, certain aspects of the techniques described above may implemented by one or more processors of a processing system executing software. The software comprises one or more sets of executable instructions stored or otherwise tangibly embodied on a non-transitory computer readable storage medium. The software can include the instructions and certain data that, when executed by the one or more processors, manipulate the one or more processors to perform one or more aspects of the techniques described above. The non-transitory computer readable storage medium can include, for example, a magnetic or optical disk storage device, solid state storage devices such as Flash memory, a cache, random access memory (RAM) or other non-volatile memory device or devices, and the like. The executable instructions stored on the non-transitory computer readable storage medium may be in source code, assembly language code, object code, or other instruction format that is interpreted or otherwise executable by one or more processors.

A computer readable storage medium may include any storage medium, or combination of storage media, accessible by a computer system during use to provide instructions and/or data to the computer system. Such storage media can include, but is not limited to, optical media (e.g., compact disc (CD), digital versatile disc (DVD), Blu-Ray disc), magnetic media (e.g., floppy disc, magnetic tape, or magnetic hard drive), volatile memory (e.g., random access memory (RAM) or cache), non-volatile memory (e.g., read-only memory (ROM) or Flash memory), or microelectromechanical systems (MEMS)-based storage media. The computer readable storage medium may be embedded in the computing system (e.g., system RAM or ROM), fixedly attached to the computing system (e.g., a magnetic hard drive), removably attached to the computing system (e.g., an optical disc or Universal Serial Bus (USB)-based Flash memory), or coupled to the computer system via a wired or wireless network (e.g., network accessible storage (NAS)).

Note that not all of the activities or elements described above in the general description are required, that a portion of a specific activity or device may not be required, and that one or more further activities may be performed, or elements included, in addition to those described. Still further, the order in which activities are listed are not necessarily the order in which they are performed. Also, the concepts have been described with reference to specific embodiments. However, one of ordinary skill in the art appreciates that various modifications and changes can be made without departing from the scope of the present disclosure as set forth in the claims below. Accordingly, the specification and figures are to be regarded in an illustrative rather than a restrictive sense, and all such modifications are intended to be included within the scope of the present disclosure.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims. Moreover, the particular embodiments disclosed above are illustrative only, as the disclosed subject matter may be modified and practiced in different but equivalent manners apparent to those skilled in the art having the benefit of the teachings herein. No limitations are intended to the details of construction or design herein shown, other than as described in the claims below. It is therefore evident that the particular embodiments disclosed above may be altered or modified and all such variations are considered within the scope of the disclosed subject matter. Accordingly, the protection sought herein is as set forth in the claims below.

What is claimed is:
1. A method comprising:
generating a first electromagnetic (EM) pose based on EM field magnitude values indicative of a first pose of an EM transmitter in relation to an EM receiver;
generating a first sensor pose based on sensor data received from a line-of-sight pose tracking system, wherein the line-of-sight pose tracking system comprises one of a sonic pose tracking system, a radiated electrical pose tracking system, and an optical pose tracking system; and identifying a first combined pose based on a first weighted combination of the first EM pose and the first sensor pose, the first weighted combination including a weighted sum of the first EM pose and the first sensor pose.

2. The method of claim 1, wherein the first weighted combination is based on a first set of weights, and the first combined pose is generated at a first time, and further comprising:

adjusting the first set of weights in response to detecting a degradation in one of the field magnitude values and the sensor data;

generating a second EM pose based on the EM field magnitude values indicative of a second pose of the transmitter in relation to the receiver;

generating a second sensor pose based on the sensor data received from a line-of-sight pose tracking system; and identifying a second combined pose at a second time based on a second weighted combination of the second EM pose and the second sensor pose, the second weighted combination based upon the adjusted set of weights.

3. The method of claim 2, wherein the degradation comprises one of occlusion, reduced signal-to-noise-ratio, multipath, signal interference, increased noise, increased latency, increased drift, reduced accuracy, out of bounds from the field of view, and magnetic distortion.

4. The method of claim 1, wherein the EM receiver is affixed to one of a transmitter or receiver of the line-of-sight pose tracking system.

5. The method of claim 1, wherein the EM transmitter is affixed to one of a transmitter or receiver of the line-of-sight pose tracking system.

6. The method of claim 1, wherein the line-of-sight pose tracking system comprises an LED constellation tracking system.

7. The method of claim 1, wherein the line-of sight pose tracking system comprises a lighthouse tracking system.

8. The method of claim 1, wherein the line-of-sight pose tracking system comprises an ultrasonic tracking system.

9. The method of claim 1, wherein the line-of-sight pose tracking system comprises a camera tracking system.

10. The method of claim 1, wherein the line-of-sight pose tracking system comprises a radiated electrical tracking system.

11. A tracking system, comprising:

an electromagnetic (EM) tracking system configured to generate a first EM pose based on EM field magnitude values indicative of a first pose of an EM transmitter in relation to an EM receiver;

a line-of-sight pose tracking system configured to generate a first sensor pose based on sensor data, wherein the line-of-sight pose tracking system comprises one of a sonic pose tracking system, a radiated electrical pose tracking system, and an optical pose tracking system; and a processor configured to identify a first combined pose based on a first weighted combination of the first EM pose and the first sensor pose, the first weighted combination including a weighted sum of the first EM pose and the first sensor pose.

12. The tracking system of claim 11, wherein the first weighted combination is based on a first set of weights, and the first combined pose is generated at a first time, and wherein:

the processor is configured to adjust the first set of weights in response to detecting a degradation in one of the field magnitude values and the sensor data;

the EM tracking system is configured to generate a second EM pose based on the EM field magnitude values indicative of a second pose of the EM transmitter in relation to the EM receiver;

the line-of-sight pose tracking system is configured to generate a second sensor pose based on the sensor data received from a line-of-sight pose tracking system; and the processor is configured to identify the second pose at a second time based on a second weighted combination of the second EM pose and the second sensor pose, the second weighted combination based upon the adjusted set of weights.

13. The tracking system of claim 11, wherein the EM transmitter is affixed to one of a transmitter or receiver of the line-of-sight pose tracking system.

14. The tracking system of claim 11 wherein the EM receiver is s affixed to one of a transmitter or receiver of the line-of-sight pose tracking system.

15. The tracking system of claim 11, wherein the line-of-sight pose tracking system comprises an LED constellation tracking system.

16. The tracking system of claim 11, wherein the line-of sight pose tracking system comprises a lighthouse tracking system.

17. The tracking system of claim 11, wherein the line-of-sight pose tracking system comprises an ultrasonic tracking system.

18. The tracking system of claim 11, wherein the line-of-sight pose tracking system comprises a camera tracking system.

19. A method, comprising:

while an electromagnetic (EMS tracking system is in a low-power mode, the low-power mode being one of a sleep mode and an off mode, generating a first sensor pose based on sensor data received from a line-of-sight pose tracking system, wherein the line-of-sight pose tracking system comprises one of a sonic pose tracking system, a radiated electrical pose tracking system, and an optical pose tracking system;

in response to identifying a degradation in the sensor data, changing a power mode of the EM tracking system from the low-power mode to an active mode; and while the EM tracking system is in the active mode, generating a first EM pose based on EM field magnitude values indicative of a first pose of an EM transmitter in relation to an EM receiver.

20. The method of claim 19, further comprising:

while the EM tracking system is in the active mode:

generating a second sensor pose based on sensor data received from the line-of-sight pose tracking system; and identifying a first combined pose based on a first weighted combination of the first EM pose and the second sensor pose.

21. A method, comprising:

while a line-of-sight pose tracking system is in a low-power mode, the low-power mode being one of a sleep mode and an off mode, generating a first electromagnetic (EM) pose based on EM field magnitude values indicative of a first pose of an EM transmitter in relation to an EM receiver, wherein the line-of-sight pose tracking system comprises one of a sonic pose tracking system, a radiated electrical pose tracking system, and an optical pose tracking system;

in response to identifying a degradation in the EM field magnitude values data, changing a power mode of the line-of-sight pose tracking system from the low-power mode to an active mode; and while the line-of-sight pose tracking system is in the active mode, generating a first sensor pose based on sensor data received from the line-of-sight pose tracking system.

22. The method of claim 21, further comprising:

while the line-of-sight tracking system is in the active mode:

generating a second EM pose based on the EM field magnitude values; and identifying a first combined pose based on a first weighted combination of the second EM pose and the first sensor pose.

* * * * *